US010041086B2

(12) United States Patent
Sawant et al.

(10) Patent No.: US 10,041,086 B2
(45) Date of Patent: Aug. 7, 2018

(54) METHOD FOR PRODUCTION OF TRANSGENIC COTTON PLANTS

(71) Applicant: COUNCIL OF SCIENTIFIC & INDUSTRIAL RESEARCH, New Delhi (IN)

(72) Inventors: Samir Viswanath Sawant, Lucknow (IN); Rajiv Kumar Tripathi, Lucknow (IN); Asif Idris, Lucknow (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 160 days.

(21) Appl. No.: 15/028,393

(22) PCT Filed: Oct. 13, 2014

(86) PCT No.: PCT/IN2014/000651
 § 371 (c)(1),
 (2) Date: Apr. 8, 2016

(87) PCT Pub. No.: WO2015/052732
 PCT Pub. Date: Apr. 16, 2015

(65) Prior Publication Data
 US 2016/0340687 A1    Nov. 24, 2016

(30) Foreign Application Priority Data
 Oct. 11, 2013   (IN) .......................... 3041/DEL/2013

(51) Int. Cl.
 *A01H 5/00*    (2018.01)
 *C12N 15/82*    (2006.01)
 *C07K 14/415*    (2006.01)

(52) U.S. Cl.
 CPC ........ *C12N 15/8261* (2013.01); *C07K 14/415* (2013.01); *C12N 15/82* (2013.01); *Y02A 40/146* (2018.01)

(58) Field of Classification Search
 None
 See application file for complete search history.

(56) References Cited

U.S. PATENT DOCUMENTS

| 5,880,110 | A | 3/1999 | Kasukabe et al. |
| 2009/0138981 | A1* | 5/2009 | Repetti ................ C07K 14/415 800/263 |
| 2010/0269230 | A1 | 10/2010 | Fincher et al. |

FOREIGN PATENT DOCUMENTS

| WO | 2011025840 A1 | 3/2011 | |
| WO | WO-2011025840 A1 * | 3/2011 | ......... C12N 15/8216 |

OTHER PUBLICATIONS

Chaudhary et al. (Plant Cell Rep., 21:955-960, 2003) (Year: 2003).*
Dyson 1999, PNAS, 96(11): 5929-5936; Pinstrup-Andersen et al 1999, World Food Prospects: Critical issues for the Early Twenty-First Century, in 2020 Vision Food Policy Report.
"The Effects of Plant Growth Substances on in vitro Fiber Development from Fertilized Cotton Ovules" Beasley and Ting (Amer. J. Bot., 60(2): 130-139 vol. 30, No. 2 (1973).
"Suppression of Sucrose Synthase Gene Expression Represses Cotton Fiber Cell Initiation, Elongation, and Seed Development" Yong-Ling Ruan et al, The Plant Cell 15:952-964, 2003.
"Functional analysis of the *Arabidopsis thaliana* SBP-box gene SPL3: a novel gene involved in the floral transition." Cardon et al Plant J. 1997, 12, 367-77.
"SPL8, an SBP-Box Gene That Affects Pollen Sac Development in *Arabidopsis*" Unte et al, Plant Cell 2003, 15, 1009-1019.
"The origin of the naked grains of maize" Wang et al, Nature 2005, 436, 714-719, Sep. 2005.
"A naturally occurring epigenetic mutation in a gene encoding an SBP-box transcription factor inhibits tomato fruit ripening." Manning et al, Nat Genet. 2006, 38, 948-952.
"Prediction of Plant MicroRNA Targets" Rhoades et al., Cell 110:513-520 110:513-520, 2002.
"Detection of 91 potential conserved plant microRNAs in *Arabidopsis thaliana* and *Oryza sativa* identifies important target genes" Bonnet et al., Proc.Natl.Sci.USA 101:11511-11516, 2004.
"MicroRNAs in plants" Reinhart et al., Genes Dev. 16:1616-1626, 2002.
"A microRNA as a translational repressor of APETALA2 in *Arabidopsis* flower development." Chen, Science 303:2022-2025, 2004.
"MicroRNA Binding Sites in *Arabidopsis* Class III HD-ZIP mRNAs Are Required for Methylation of the Template Chromosome" Bao et al, 7:653-662, 2004.
"The sequential action of miR156 and miR172 regulates developmental timing in *Arabidopsis*" Wu et al, Cell 138, 750-759, Aug. 21 2009.
"The microRNA regulated SBP-box transcription factor SPL3 is a direct upstream activator of Leafy, Fruitfull, and APETALA1" Yamaguchi et al, Developmental Cell 17, 268-278, 2009.
"The C. elegans heterochronic gene lin-4 encodes small RNAs with antisense complementarity to lin-14." Lee et al, Cell 75:843-854 1993.
"Posttranscriptional regulation of the heterochronic gene lin-14 by lin-4 mediates temporal pattern formation in C. elegans." Wightman et al, Cell 75:855-862, Dec. 3, 1993.
"MicroRNAs in plants." Reinhart et al, Genes Dev. 16:1616-1626, 2002.
"Genome-wide analysis reveals rapid and dynamic changes in miRNA and siRNA sequence and expression during ovule and fiber development in allotetraploid cotton" Pang et al, Genome Biology, 2009.

(Continued)

*Primary Examiner* — Vinod Kumar
(74) *Attorney, Agent, or Firm* — Maschoff Brennan

(57) ABSTRACT

The present invention provides a method for producing transgenic Cotton plants. In one method transformed plants, that overexpress the transgene shows a phenotype that includes increased boll number, size and lint percentage in compare to the wild type plants; whereas in the second method transformed plants that reduced the transgene level produced plants with decreased number of cotton boll, size and lint percentage in compare to wild type and overexpression line both. q-RT PCR analysis showed that transgene transcript level was higher at fiber initiation stage (0DPA) after that its level decreases throughout all developmental stages.

2 Claims, 8 Drawing Sheets

(56) References Cited

OTHER PUBLICATIONS

"Gapped BLAST and PSI-BLAST: a new generation of protein database search programs." Altschul et al., Nucl. Acids Res. 25:3389-3402, Sep. 1, 1997.
"Basic local alignment search tool." Altschul et al., J. Mol. Biol. 215:403-410, Oct. 5, 1990.
"Amino acid substitution matrices from protein blocks" Henikoff et al, Proc. Natl. Acad. Sci. USA 89:10915-10919, 1992.
"Applications and statistics for multiple high-scoring segments in molecular sequences" Karlin et al., Proc. Natl. Acad. Sci. USA 90:5873-5877, 1993.
"Identification and evaluation of new reference genes in Gossypium hirsutum for accurate normalization of real-time quantitative RT-PCR data" Artico et al. 2010.
"Molecular characterisation of the *Arabidopsis* SBP-box genes" Cardon G et al., Gene, Elsevier, Amsterdam vol. 237, No. 1, Sep. 3, 1999.

\* cited by examiner (b) Cotton boll yeild
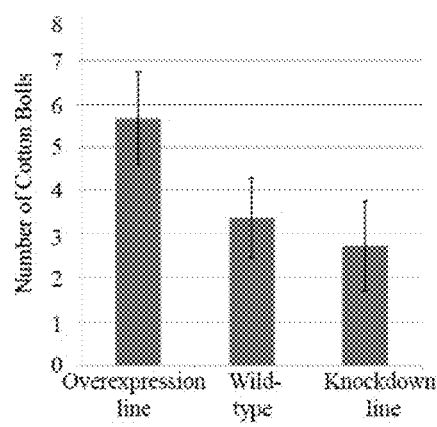
(c) Lint cotton weight
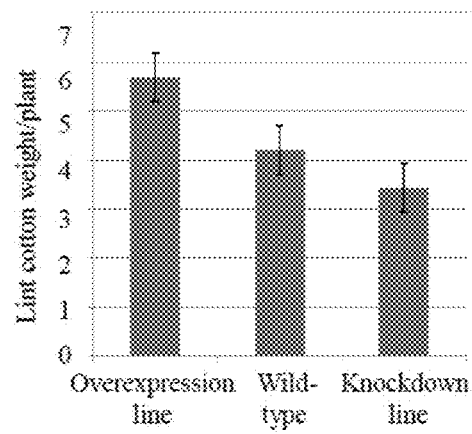
(d) Seed cotton weight
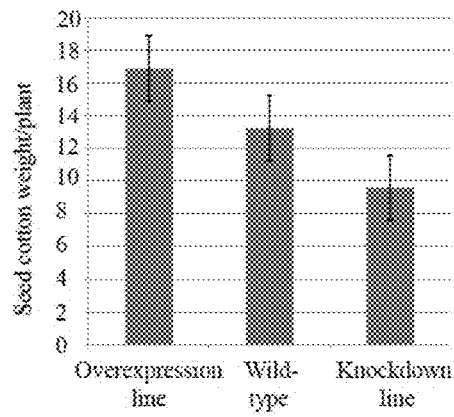
Figure 7 (b-d)

SEQUENCE LISTING

<160> NUMBER OF SEQ ID NOS: 6

<210> SEQ ID NO 1
<211> LENGTH: 549
<212> TYPE: DNA
<213> ORGANISM: Artificial Sequence
<220> FEATURE:
<223> OTHER INFORMATION: Nucleotide sequence of the complete ORF of SPL5 gene without miR156 target site

<400> SEQUENCE: 1

```
atgaataagg atttcatagc tgaagaactt gacaatgaca tgcaagaaga agaagaagaa      60
ggtgttgggg gtgatcatgg tttcccagat gatgaaaaga agaagaaagg ttatggaagg     120
agaggagccg ctggtggcgg tggtggggtg tcgccgcctg cttgtcaagt ggaaaaatgt     180
gggcttgatt tatctgatgc caagcgatac cacaggcgcc ataaggtgtg tgagattcat     240
gccaaggcgc catttgtggt tgttgctggt ctcaggcaac gcttctgtca acaatgcagc     300
agattccatg agctaccgga gttcgatgaa gcaaaacgga gctgtcgaag gcggttggcc     360
gggcataacg aaaggcgtcg gaagagctca gctgaatcat catcagcagc agaaagttca     420
aatcgcagag ggatgatgat cagtgctcaa ctgaaagagt ctcattacct agctgatgat     480
caaagagcca gagtcaatcc aatggcaatc catggcagtt catcttttaa gcgttcccaa     540
atcagataa                                                             549
```

<210> SEQ ID NO 2
<211> LENGTH: 182
<212> TYPE: PRT
<213> ORGANISM: Artificial Sequence
<220> FEATURE:
<223> OTHER INFORMATION: Amino acid sequence of SPL5 protein

<400> SEQUENCE: 2

```
Met Asn Lys Asp Phe Ile Ala Glu Glu Leu Asp Asn Asp Met Gln Glu
1               5                   10                  15

Glu Glu Glu Glu Gly Val Gly Gly Asp His Gly Phe Pro Asp Asp Glu
            20                  25                  30

Lys Lys Lys Lys Gly Tyr Gly Arg Arg Gly Ala Ala Gly Gly Gly Gly
        35                  40                  45

Gly Val Ser Pro Pro Ala Cys Gln Val Glu Lys Cys Gly Leu Asp Leu
    50                  55                  60

Ser Asp Ala Lys Arg Tyr His Arg Arg His Lys Val Cys Glu Ile His
65                  70                  75                  80

Ala Lys Ala Pro Phe Val Val Val Ala Gly Leu Arg Gln Arg Phe Cys
                85                  90                  95

Gln Gln Cys Ser Arg Phe His Glu Leu Pro Glu Phe Asp Glu Ala Lys
            100                 105                 110

Arg Ser Cys Arg Arg Arg Leu Ala Gly His Asn Glu Arg Arg Lys
        115                 120                 125

Ser Ser Ala Glu Ser Ser Ala Ala Glu Ser Ser Asn Arg Arg Gly
    130                 135                 140

Met Met Ile Ser Ala Gln Leu Lys Glu Ser His Tyr Leu Ala Asp Asp
145                 150                 155                 160

Gln Arg Ala Arg Val Asn Pro Met Ala Ile His Gly Ser Ser Ser Phe
                165                 170                 175

Lys Arg Ser Gln Ile Arg
            180
```

```
<210> SEQ ID NO 3
<211> LENGTH: 25
<212> TYPE: DNA
<213> ORGANISM: Artificial Sequence
<220> FEATURE:
<223> OTHER INFORMATION: SPL5-Forward Primer

<400> SEQUENCE: 3
atgaataagg atttcatagc tgaag                                  25

<210> SEQ ID NO 4
<211> LENGTH: 20
<212> TYPE: DNA
<213> ORGANISM: Artificial Sequence
<220> FEATURE:
<223> OTHER INFORMATION: SPL5-Reverse primer

<400> SEQUENCE: 4
ttatctgatt tgggaacgct                                        20

<210> SEQ ID NO 5
<211> LENGTH: 20
<212> TYPE: DNA
<213> ORGANISM: Artificial Sequence
<220> FEATURE:
<223> OTHER INFORMATION: Primer for analysis of transgenic plant gene
      expressions

<400> SEQUENCE: 5
acacagccat cggtccagac                                        20

<210> SEQ ID NO 6
<211> LENGTH: 23
<212> TYPE: DNA
<213> ORGANISM: Artificial Sequence
<220> FEATURE:
<223> OTHER INFORMATION: Primer for analysis of transgenic plant gene
      expressions

<400> SEQUENCE: 6
gacgtctgtc gagaagtttc tga                                    23
```

METHOD FOR PRODUCTION OF TRANSGENIC COTTON PLANTS

TECHNICAL FIELD OF THE INVENTION

The present invention relates to a method for production of transgenic cotton plants. The invention particularly relates to a Squamosa Promoter Binding like Transcription Factor 5 (SPL5) involved in the modulation of boll density (boll number and size) and lint percentage in cotton. Methods and means are provided to alter fiber quality and quantity by increasing or decreasing the SPL5 level thereby improving the cotton yield and increasing the breeding of such plants.

SEQUENCE LISTING

The instant application contains a Sequence Listing which has been submitted electronically in a text file and is hereby incorporated by reference in its entirety. Said text copy, named C1805_10005US01_SL.txt and is 4,000 bytes in size.

BACKGROUND AND PRIOR ART OF THE INVENTION

Three main factors namely global factors, population growth and the adoption of crops for biofuels create the necessity to develop novel approaches to increase crop yield. Crop productivity and yield enhancement in recent years are being achieved by genotype improvement through classical breeding, use of nitrogen fertilizer and pesticide, right agronomic way. Due to rapid population growth, income growth in developing countries, limited availability of land and climate change, achieving sustainable food security will require technological advances in agronomic practices, breeding and agricultural biotechnology (Dyson 1999, PNAS, 96(11): 5929-5936;Pinstrup-Anderson et al 1999, World Food Prospects: Critical issues for the Early Twenty-First Century, in 2020 Vision Food Policy Report). Cotton contributes natural fiber for the worldwide textile industry; therefore, dissecting its biological properties is a very important scientific objective. Although it is not easy to improve both yield and fiber quality concurrently; the yield of cotton fibers, usually known as cotton lint, is usually negatively associated with fiber quality. Aim to be achieved include increased cotton boll density, lint percentage, fiber length and strength. Presently cotton fiber quality can be improved by three types. First is by cross breeding but this method need much more time. Second is the use of fatty acids and plant hormones. Plant hormone such as Auxin or gibberellins has a promoting effect on the fiber elongation in ovule cultures {Beasley and Ting (Amer. J. Bot., 60(2): 130-139(1973), Baert et al., 1975} whereas kinetin and abscisic acid have an inhibitory effect. U.S. Pat. No. 5,880,110 produces cotton fibers with improved quality by treatment with brassinosteroids. Yong-Mei Qin et al., 2007 have reported that saturated very-long-chain fatty acids (VLC-FAs; C20:0 to C30:0) exogenously applied in ovule culture medium significantly promoted cotton (Cotton) fiber cell elongation. The third one is by doing genetic manipulation. In recent years genetic manipulations have been made successful variety improvement in plants such as rice, tomato, maize etc. Therefore if a gene related with fiber development is transformed into cotton and overexpressed, it may play crucial role in the improvement of quality or yield of cotton fiber. At present, however, only the few studies have been made on cotton plants to improve the characteristics or yields of fiber such as by introduction of a BT toxin (Bacillus thuringiensis) gene into cotton to improve insect resistance, to improve herbicide (Glyphosate) resistance by introduction of 5-enol-pyruvilsshikimic acid 3-phosphate synthetase gene in cotton. There are few reports related to the method for genetically engineering a fiber producing plant and the identification of cDNA clones useful for identifying fiber genes in cotton. U.S. Pat. No. 5,597,718. Complete ORF sequence from these isolated genes is used in sense or antisense orientation to modulate the transgenic fiber producing plants. Suppression of sucrose synthase gene expression in cotton leads to reduced cell fiber length and smaller and fewer fiber cells (Yong-Ling Ruan et al, Plant Cell 15:952-964, 2003)

Identification and manipulation of specific genes in cotton that play a significant role in determining yield could provide a path to obtain substantial yield increase in a relatively short time.

SPL5 is a plant specific transcription factor which belongs to the SBP superfamily. Members of this superfamily share a highly conserved DNA binding SBP domain and are involved in various function such as flowering, early stages of microsporogenesis and megasporogenesis, development of normal plant architecture maize kernel development, tomato fruit ripeness, and shoot maturation in Arabidopsis (Cordon et. al Plant J. 1997, 12, 367-77; Unte et al, Plant Cell 2003, 15, 1009-1019; Wang et al, Nature 2005, 436, 714-719; Manning et al, Nat. Genet. 2006, 38, 948-952).

SPLs are among the transcription factors subjected to microRNA (miRNA) regulation. miR156 negatively regulates SPL gene family in Arabidopsis. miRNA originate from distinct loci within a plant's genome and are short non coding RNAs (20-24 nucleotide long) whose function is to repress the expression of defined target genes (Rhoades et al., Cell 110:513-520 110:513-520, 2002; Bonnet et al., Proc. Natl. Sci. USA, 101:11511-11516, 2004;Reinhart et al., Genes Dev. 16:1616-1626, 2002). miRNAs are produced from longer precursor molecules by a Dicer-like (DCL) ribonuclease and get incorporated into ribonucleoprotein silencing complexes that effect repression of target mRNAs via base pairing of the small RNA and its target mRNA (Chen, Science 303:2022-2025, 2004; Bao et al, Dev. Cell. 7:653-662, 2004). A number of researches have supported that SPL mRNAs are repressed by miR156 and this repression produces late flowering phenotype (Wu et al, Cell 138,750-759, 2009; Yamaguchi et al, Developmental Cell 17, 268-278, 2009).

Limitations in Prior Art

Presently no gene has been identified which causes significant increase in the boll number, size and increase in lint yield in cotton. Hence there was need to identify cotton boll density specific gene. In this present invention, we have identified a gene from Cotton which causes increase in number of cotton boll. The gene also causes significant increase in boll size and increased lint percentage. The prior art lacks identification of gene responsible for above said traits in cotton.

OBJECTIVE OF THE INVENTION

The main objective of the invention is to provide a method for production of transgenic cotton plants wherein the plant has increased number, size and lint yield.

SUMMARY OF THE INVENTION

Accordingly, the present invention provides a method for production of transgenic cotton plants.

The present invention provides plants comprising a plant growth and/or development nucleic acid/gene of the present invention, as well as compositions and methods for producing such plants.

In a further embodiment, the full-length plant growth and/or development nucleic acid/gene is operatively associated with a cauliflower mosaic virus 35S constitutive promoter (CaMV35S) and optionally with a polyA sequence, wherein the plants of the present invention have an increase in boll number, boll size and lint percentage as compared with a wild-type plant which does not comprise the nucleic acid/gene.

In another embodiment, truncated plant growth and/or development nucleic acid/gene is operatively associated with a constitutive promoter and intron with a optionally polyA sequence, wherein the plants have a decrease in boll number, boll size and lint percentage as compared with a wild type plant which does not comprise the nucleic acid/gene.

In one embodiment, the resultant increase in boll number, size and lint percentage leads to increased yield.

The present invention also provides transformed cells, tissue cultures and/or plant parts comprising the modified plant growth and/or development nucleic acid/gene of the present invention. The transformed cell, tissue culture or plant part can be derived from regenerable cells from embryos, protoplasts, meristemetic cells, callus, pollen, leaves, anthers, stems, petioles, roots, root tips, fruits, seeds, flowers, cotyledons, or hypocotyls.

In one embodiment, the modified plant growth and/or development nucleic acid/gene has no miRNA binding site.

In one embodiments, the modified plant growth and/or development nucleic acid/gene is operatively associated with a constitutive promoter and optionally a polyA sequence, wherein the transformed cell, tissue culture or plant part can give rise to a transgenic plant demonstrating an increase in boll number, size and lint percentage as compared with a wild-type plant or a plant which comprise the silenced plant growth and/or development nucleic acid/gene.

In some further embodiments, the SPL5 gene is from cotton.

The present methods and compositions increase boll number, size and lint percentage in plants. In some embodiments, the present methods and compositions relate to the use of a modified growth and/or development regulatory nucleic acid/gene that is over-expressed in a plant. In particular, the present methods and compositions relate to the use of a miRNA-resistant growth and/or development regulatory nucleic acid/gene comprising under the control of an appropriate constitutive promoter. In some embodiments, the plant is a transgenic plant, and the growth and/or development regulatory gene is a transgene in the transgenic plant. Over expression of the modified gene in a plant provides for increased boll number, size and lint percentage in the transgenic plant when compared with the wild-type plant; whereas, knockdown expression of growth and/or development regulatory gene produced decreased boll number, size and lint percentage in the transgenic plant when compared with the wild-type plant.

The present disclosure also provides methods for selecting for a nucleic acid/gene that increases plant yield when functionally associated with a constitutive promoter; wherein the methods comprise constructing an expression vector comprising a nucleic acid/gene associated with plant growth and/or development having no miRNA binding site, transfecting a plant cell with the expression vector to form a transgenic plant; growing the transgenic plant and selecting those transgenic plants that have an increased yield.

In another embodiment the invention provides a method for production of transgenic cotton plants useful to obtain increase in yield of boll number and size comprising steps of:
 a) Providing cotton genomic DNA and cDNA having the SPL5 gene of sequence I.D. 1;
 b) Amplifying SPL5 gene from the DNA obtained in step (a) using primer sequence of sequence I.D. 3 and 4.
 c) Cloning the amplified gene obtained in step (b) into a suitable expression vector operably linked to promoter selected from but not restricted to FBP7, Actin, TA29 and CaMV35S
 d) Transforming the vector into cotton plant using *Agrobacterium* mediated transformation to obtain transgenic cotton plant having increase in yield of boll number and size.

In yet another embodiment the invention provides a recombinant construct useful for increasing the yield of boll number and size in cotton of transgenic cotton plant comprising a plant growth & development regulator SPL5 gene of sequence I.D.1 operably linked to promoter selected from but not restricted to FBP7, Actin, TA29 and CaMV35S for transforming cotton plants.

In yet another embodiment the invention provides a process of cotton transformation for producing transgenic plants containing gene of sequence I.D. 1 comprising steps;
 A) Providing the construct containing Seq Id no. 1;
 B) Transforming *Agrobacterium* strain GV3101 with the construct obtained in step (A);
 C) Transforming the cotton plant with *Agrobacterium* obtained in step (B);
 D) Regenerating transformed cotton plants obtained in step (C).

In yet another embodiment the invention provides a construct for transformation of cotton plants, comprising nucleotide having seq ID no. 1 encoding a polypeptide of seq. I.D. no. 2.

In yet another embodiment the invention provides Primers for isolation of SPL5 gene, having seq id no. 3 and 4.

BRIEF DESCRIPTION OF THE DRAWINGS

FIG. 5a is overexpression line screening and shows that Lane 1, 2, 4, 5, 6, 8, 10, 11 are positive overexpression lines. Lane 3 and 9 are negative lines. Lane 12 positive control and lane 13 is negative control. Lane 7, is 100 bp marker. FIG. 5b is knockdown line screening which shows lane 1, 4, 5, and 9 are positive knockdown lines whereas lane 2, 3, 6, and 8 are negative lines. Lane 7 is 100 bp marker, lane 10 is positive control and lane 11 is negative control.

FIG. 7b shows higher number of the cotton bolls in overexpression line containing CaMV35S-SPL5 chimeric gene compared to wild type plants, whereas, knockout line shows lower number of the cotton bolls compared to the wild type plants, In FIG. 7c, lint quantity is shown and in FIG. 7d, seed cotton with lint is shown.

DETAILED DESCRIPTION OF THE INVENTION

Figure 1:
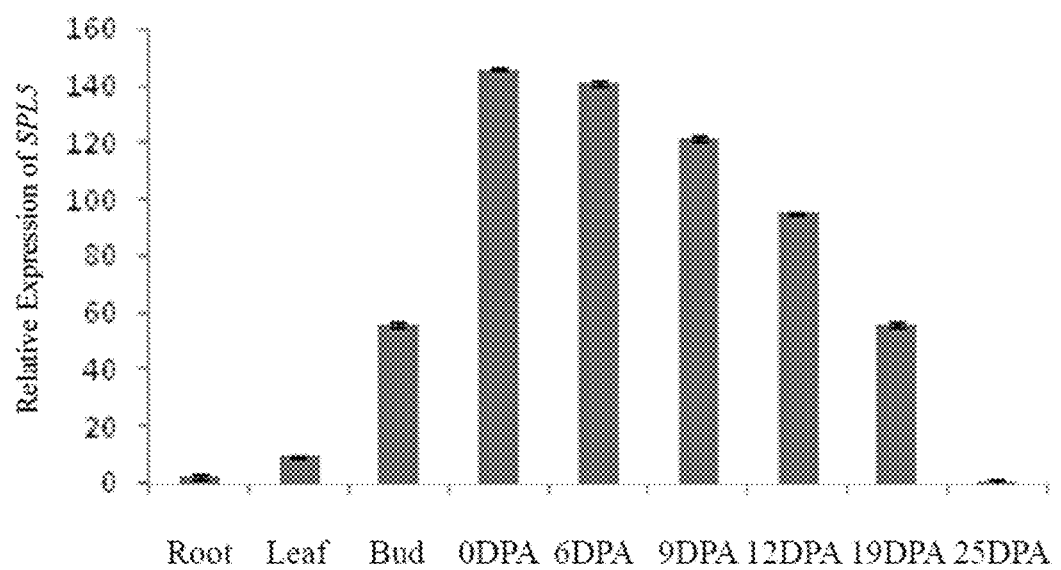
FIG. 1. Expression analysis of the SPL5 gene by Real Time PCR at different developmental stages (Root, Leaf, Bud, 0, 6, 9, 12, 19 and 25 DPA) of cotton. Highest expression was found at fiber initiation stage (0 DPA) of fiber development and after that its expression goes down.

Unless defined otherwise, all technical and scientific terms used herein have the same meaning as commonly understood by one of ordinary skill in the art to which the compositions and methods described herein belong. Although any methods and materials similar to those described herein can be used in the practice or testing of the present methods and materials, only exemplary methods and materials are described. Real Time PCR (qRT-PCR) is a very accurate measurement technique for expression analysis of genes in molecular biology. qRT-PCR is used to quantify the expression of a particular gene with reference to a housekeeping gene, which is used as a control. The present invention provides a plant growth and development gene (SPL5) identified from microarray data of Cotton. Four SPL family members were selected for functional validation. Real Time PCR of said SPLs was done in root, leaf, bud and six different fiber development stages namely 0 DPA (Zero Day Post Anthesis), 6 DPA, 9 DPA, 12 DPA, 19 DPA, 25 DPA and result showed that only SPL5 out of four SPLs was fiber specific (Example 1).Therefore, this gene was selected for functional validation. The SPL5 transcript encodes a sequence of 731 base pairs having 1 to549 nucleotides coding sequence with a stop codon at 549 nucleotide and 3' untranslated region from base pair 550 to 731 having a miRNA binding site at 577 to 594.

siRNAs were first discovered in plants (Hamilton and Baulcombe, Science 286:950-952, 1999; Llave et al, Plant Cell 14:1605-1619, 2002) and play roles in defense against viruses, suppression of expression from transgenes or transposons, establishment of heterochromatin, and post-transcriptional regulation of mRNAs.

MiRNAs are small (20-24 nt) RNA molecules derived from non-coding miRNA genes found in many organisms (Lee et al, Cell 75:843-854 1993; Wightman et al, Cell 75:855-862, 1993; Reinhart et al, Genes Dev. 16:1616-1626, 2002). miRNAs base-pair with target mRNA sequences in their miRNA binding sites and this binding leads to the down regulation of target mRNA expression. The first case of miRNA regulation was discovered in Caenorhabditis elegans (Lee et al, Cell 75:843-854, 1993; Wightman et al, Cell 75:855-862, 1993), and since that time, many more miRNAs have been found in diverse eukaryotes, with the exception of Saccharomyces cerevisiae. SPL transcription factor family members have microRNA (miRNA) binding sites in their 3' UTR that are complementary to miRNAs 156 in the cotton genome. The evolutionarily conserved miRNAs are classified into gene families. Thus there are four miRNA 156 (a-d) genes in the cotton genome.

siRNA and miRNA are chemically and functionally similar. Both are short non-coding RNAs (20-24 nucleotides (nt) in length) whose function is to repress the expression of defined target genes in animals and plants. Both RNA species are generated from longer precursor molecules by a Dicer-like (DCL) ribonuclease and get incorporated into ribonucleoprotein silencing complexes that effect repression of target mRNAs via base pairing of the small RNA and its target mRNA. The silencing complexes require the activity of Argonaut proteins. Repression may occur by cleavage of the target mRNA or inhibition of translation (post-transcriptional regulation) or by methylation of the target gene (transcriptional regulation) (Chen, Science 303:2022-2025, 2004; Bao et al., Dev. Cell. 7:653-662, 2004).

Studies have also been done, both in vivo and in vitro, to show that SPL mRNAs are cleaved in the presence of miRNA 156 and that this cleavage is dependent upon the miRNA binding site sequence (Pang et al, Genome Biology, 2009). 5' RACE experiments have also shown that target mRNA is cleaved at a specific position within the miRNA binding site (Wu et. al, Cell 138, 750-759, 2009) and that this cleavage is abolished in the miRNA-resistant SPL mutant.

Plants that over express the Cotton SPL5 transgene produced higher boll number, size and lint yield. There are two straightforward interpretations of these results: i) the SPL transgene functions at the protein level to cause the boll and lint yield increase, or ii) the SPL transgene functions at the transcriptional level to cause the boll and lint yield increase.

The protein model (i.e., above) hypothesizes that SPL is transcribed from the transgene into mRNA and then subsequently translated into protein. It is the excess expression of SPL protein from the transgene that is believed to lead to the boll and lint yield increase, presumably by the action of excess SPL protein on inhibition or activation of downstream target genes or by sequestration of other transcriptional factors.

To distinguish between the opposing protein and transcript models, the present invention generated transgenic events. In one embodiment the event generated a plant carrying transgene that code for a full-length SPL protein and do not contain miRNA binding site. Cotton SPL5 coding sequence without miRNA binding site was engineered containing a translation termination codon at the end of the coding sequence (Example 2).

In another embodiment, the transgene was silenced by its homologous double stranded small interfering RNA (siRNA) through a process known as RNA interference (RNAi). Plants having the silenced SPL5 transgene decrease in boll number, size and lint percentage in compare to the wild type or a plant which do not comprise the silenced plant growth and development gene (Example 3).

In the embodiment of the invention, the nucleotide sequence encoding an SPL5 gene is represented in sequence SEQ. I.D. NO.1.

In the other embodiment of the invention, the amino acid sequence of SPL5 protein is shown in sequence SEQ. I.D. NO. 2.

A number of plant genes have been shown by over expression or suppression analysis to play roles in growth and/or development. Examples of some, but not all, of the genes that are known to be involved in growth and/or development and that can be used or tested in the methods of the present invention are discussed herein below. The Arabidopsis CAP gene, sucrose synthase gene, histone deacetylase 1 gene, E2Fc, BKI gene, BRII gene, Argos-Like (ARL) gene.

SPLs in plants have been described previously such as in patent publication WO/2011/025840. A SPL gene is involved in the regulation of flower development (Cardon et. al Plant J. 1997, 12, 367-77; Wu et. al, Cell 138, 750-759, 2009), maize kernel development (Wang et al, Nature 2005, 436, 714-719), tomato fruit ripening (Manning et al, Nat. Genet. 2006, 38, 948-952) etc.

A plant growth and/or development related gene is a gene that plays a role in determining growth rate, overall size, tissue size, or tissue number of a plant or plays a role in the plant developmental program leading to determination of tissue identity and morphology. Such growth and development related genes are identified when modification of their function by mutation, over expression, or suppression of expression results in altered plant growth rate, overall plant size, tissue size or number, or altered development. Plant growth and/or development related genes can exert their effects through a number of mechanisms some of which include regulation of cell cycle, plant hormone synthesis/breakdown pathways, sensitivity to plant hormones, cell wall biosynthesis, cell identity determination, and the like. The plant growth and/or development related genes suitable for use in the disclosed methods also comprise a miRNA binding site and the expression and/or activity of the gene is controlled by the binding of one or more miRNA.

The term "vector" refers to a piece of DNA, typically double-stranded, which may have inserted into it a piece of foreign DNA. The vector may be of plasmid origin. Vectors contain "replicon" polynucleotide sequences that facilitate the autonomous replication of the vector in a host cell.

The term "plant" includes whole plants, plant organs, (e.g., leaves, stems, flowers, roots, and the like), seeds and plant cells (including tissue culture cells) and progeny of same. The class of plants which can be used in the methods of the present disclosure is generally as broad as the class of higher plants amenable to transformation techniques, including both monocotyledonous and dicotyledonous plants, as well as certain lower plants such as algae, e.g., cyanobacteria, and the like. It includes plants of a variety of ploidy levels, including polyploid, diploid, hexaploid, tetraploid, haploid, and the like.

The terms "SPL5 gene" or "SPL5 transgene" are used herein to mean any polynucleotide sequence that encodes or facilitates the expression and/or production of a SPL5 protein. Thus the terms "SPL5 gene" or "SPL5 transgene" can include sequences that flank the SPL5 protein encoding sequences. For example, the sequences can include those nucleotide sequences that are protein encoding sequences (exons), intervening sequences (introns), the flanking 5' and 3' DNA regions that contain sequences required for normal expression of the SPL5 gene (i.e., the promoter and polyA addition regions, respectively, and any enhancer sequences).

The term 'lint percentage' means weight of lint cotton obtained in sample/weight of seed cotton in sample ×100.

The term "substantial identity" of polynucleotide sequences means that a polynucleotide comprises a sequence that has at least 60% sequence identity, typically at least 70%, more typically at least 80% and most typically at least 90%, compared to a reference sequence using the programs described below using standard parameters. One of skill will recognize that these values can be appropriately adjusted to determine corresponding identity of proteins encoded by two nucleotide sequences by taking into account codon degeneracy, amino acid similarity, reading frame positioning and the like.

Amino acid sequence identity can be determined, for example, in the following manner. The portion of the amino acid sequence of the protein encoded by the growth and/or development associated gene, e.g., SPL5, can be used to search a nucleic acid sequence database, such as the GenBank® database, using the program BLASTP version 2.0.9 (Atschul et al., Nucl. Acids Res. 25:3389-3402, 1997). Sequence comparisons between two (or more) polynucleotides or polypeptides are typically performed by comparing sequences of the two sequences over a "comparison window" to identify and compare local regions of sequence similarity.

Another example of an algorithm that is suitable for determining percent sequence identity and sequence similarity is the BLAST algorithm, which is described in Altschul et al., J. Mol. Biol. 215:403-410, 1990. Software for performing BLAST analyses is publicly available through the National Center for Biotechnology Information web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as long as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and the speed of the alignment. The BLAST program uses as defaults a wordlength (W) of 11, the BLOSUM62 scoring matrix (see, Henikoff et al, Proc. Natl. Acad. Sci. USA 89:10915-10919, 1992) alignments (B) of 50, expectation (E) of 10, M=5, N=−4, and a comparison of both strands.

In addition to calculating percent sequence identity, the BLAST algorithm also performs statistical analysis of the similarity between two sequences (see e.g., Karlin et al., Proc. Natl. Acad. Sci. USA 90:5873-5877, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison test is less than about 0.1, more preferably less than about 0.01, and most preferably less than about 0.001. Additional methods and algorithms for sequence alignment and analysis of sequence similarity are well known to the skilled artisan.

In a particular embodiment of the present disclosure the SPL5 gene sequence used is that from Cotton.

In general, a suitable promoter is being operably linked to a plant growth and/or development associated gene and expressed using the described methods of the present invention typically has constitutive expression in all plant tissues.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, and conversely any positive traits would remain within the line also. Plant tissue culture is used widely in plant science; it also has a number of commercial applications (Example 4).

It is the excess expression of SPL protein from the transgene that is believed to lead to the boll number, size and lint percentage increase, presumably by the action of excess SPL protein on inhibition or activation of downstream target genes or by sequestration of other transcriptional factors; whereas, low expression of SPL protein from the transgene leads to decrease in boll number, size and lint percentage (Example 5).

The present invention relates to monocotyledonous or a dicotyledonous plant transformation, wherein the plant is selected from a group consisting of tobacco, cotton, rice, wheat, corn, potato, tomato, oilseed rape, alfalfa, sunflower, onion, clover, soyabean, pea.

One embodiment provides *Agrobacterium* strain selected from a group consisting of GV3101, LBA4404, EHA 101 and EHA 105.

Another embodiment provides explant selected from a group consisting of leaf, stem, root, hypocotyls and embryo.

Yet another embodiment provides a transformed plant cell comprising the recombinant construct.

Still another embodiment provides a transgenic plant transformed with the recombinant construct.

Yet another embodiment provides a plant, a plant part, a seed, a plant cell and a progeny thereof, wherein the plant, plant part, seed, plant cell, or progeny thereof comprises the recombinant construct.

A "cloning vector" is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide antibiotic or herbicide resistance.

A "binary vector" is able to replicate in both *E. coli* and *Agrobacterium tumefaciens*. It typically contains a foreign DNA in place of T-DNA, the left and right T-DNA borders, marker for selection and maintenance in both *E. coli* and *Agrobacterium tumefaciens*, a selectable marker for plants. This plasmid is said to be disarmed since its tumor-inducing genes located in the T-DNA have been removed.

A "recombinant vector" is a vector in which a foreign DNA has been inserted.

An "expression vector" is a vector in which an expression cassette has been genetically engineered.

An "expression cassette" is a DNA molecule comprising a gene that is expressed in a host cell and a promoter, driving its expression. Typically, gene expression is placed under the control of certain tissue-specific regulatory elements.

A "promoter" is a region of DNA that facilitates the transcription of a particular gene. Promoters are typically located near the genes they regulate, on the same strand and upstream (towards the 5' region of the sense strand).

The term "expression" refers to the biosynthesis of a gene product. For example, in the case of a structural gene, expression involves transcription of the structural gene into mRNA and the translation of mRNA into one or more polypeptides.

In this disclosure "transformation" is the genetic alteration of plant/bacterial cell resulting from the uptake and expression of foreign genetic material (DNA).

The term "Intron" refers to a non coding part of a DNA molecule.

The term "DPA" refers to days after anthesis and anthesis is the opening of flower.

In one embodiment cotton fiber candidate gene was identified.

In another embodiment gene was amplified from cotton.

In another embodiment expression of gene was quantified.

Yet another embodiment gene was cloned in a suitable plant overexpression vector.

Yet another embodiment gene was cloned in suitable plant knockdown vector.

Yet another embodiment overexpression and knockdown vectors were transformed into cotton through *agrobacterium* mediated.

The examples further describe the construction of an expression vector comprising an appropriate promoter and a modified gene with a role in plant growth and/or development. In particular, in some embodiments, the constitutive promoter CaMV35S was operative associated with the cotton SPL5 coding region (cds) that that comprises no miRNA binding site whereas in other case CaMV35S is associated with truncated SPL5 transcript flanking a gus intron in a RNAi expression module. These constructs were used to produce transgenic cotton plants.

EXAMPLES

The following examples are given by way of illustration therefore should not be construed to limit the scope of the invention.

Abbreviations Used:
DPA: Day Post Anthesis
q-RT PCR: Quantitative Reverse Transcription-Polymerase Chain Reaction miRNA: microRNA
SPL: Squamosa Promoter Binding like Transcription Factor Example 1

Expression Analysis of SPL5 Gene at Different Developmental Stages of Cotton

Total RNA was isolated using RNA isolation kit (Sigma-Aldrich) from field grown Cotton plants (of J.K. Agrigenetics Pvt. Ltd., Hyderabad, India) at different developmental stages namely Root, Leaf, Bud, 0 DPA, 6 DPA, 9

DPA, 12 DPA, 19 DPA, 25 DPA. After DNase I treatment (Ambion), RNA was quantified and checked for the integrity by using a Bioanalyzer 2100 (Agilent, Inc., Palo Alto, Calif., USA). 2 µg of DNase treated RNA was used for cDNA preparation using oligo dT primer by SuperScript® cDNA Synthesis Kit (Invitrogen) in 20 µl. The cDNA products were then diluted 10-fold with deionized water before use as a template in real-time PCR. The quantitative reaction was performed on ABI 7500 Real-Time PCR Detection System (Applied Biosystems) using the SYBR Green PCR Master Mix (Applied Biosystems, CA). The reaction mixture (10 µL) contained 5× SYBR Green PCR Master mix, 1 µl (10 pmol) each of the forward and reverse primers and 1µL of cDNA. All experiments were done in three biological replicates and two technical replicates. PCR amplification was performed under the following conditions: 95° C. for 20 s, followed by 40 cycles of 95° C. for 3 s and 62° C. for 30 s. The expressions of transcripts were normalized against an internal reference ubiquitine GhUBQ14 (Artico et al. 2010) gene. The relative gene expression was calculated using the $2^{\wedge -\Delta\Delta Ct}$ method. The expression of transcript was highest at 0 DPA of fiber developmental stage i.e. initiation stage of fiber development (FIG. 1).

Example 2

Construction of Over Expression Module

Figure 2:
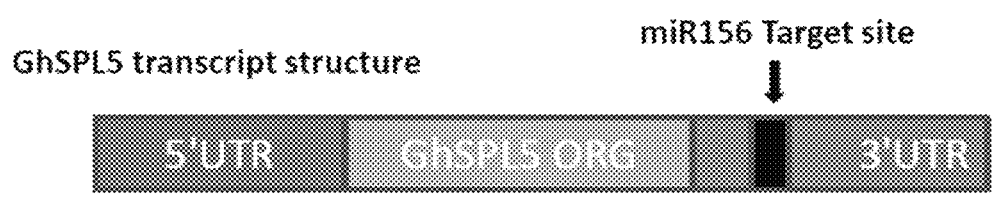
FIG. 2. Squamosa promoter binding protein-like transcription factor 5 transcript structure showing microRNA 156 target site in its 3' UTR (Untranslated) region. The miR 156 binding site distribution is schematically represented.
Figure 3:
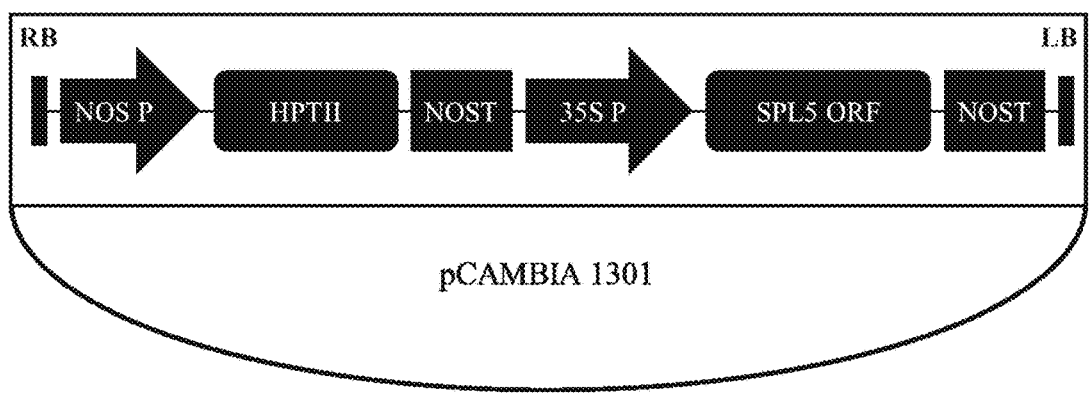
FIG. 3. The construction of full length SPL5 expression cassette. Lane 1, 2, 3, 4, 5, 6 are positive clone and lane 7 is 100 bp marker. Arrow denotes the desired band of 549 of SPL5 coding region.

Complete SPL5 gene ORF (isolated from cDNA by using primer of Sequence I.D. No. 3 and Sequence I.D. No. 4) of 549 bp (FIG. 2) was cloned into EcoRV digested $Sk^{30}$ and then sub-cloned into NcoI/BstEII digested pCAMBIA 1301 binary vector. The resultant pCAMBIA 1301 (of Cambia Institute, Canberra, Australia) carrying the Overexpression module was transformed into cotton via *Agrobacterium tumefaciens* strain GV3101 (DNA Cloning Services; Hamburg, Germany) following the modified protocol (Cangelosi et al., 1991) (FIG. 3).

Example 3

Construction of Knock Down (RNAi) Expression Module

Figure 4:
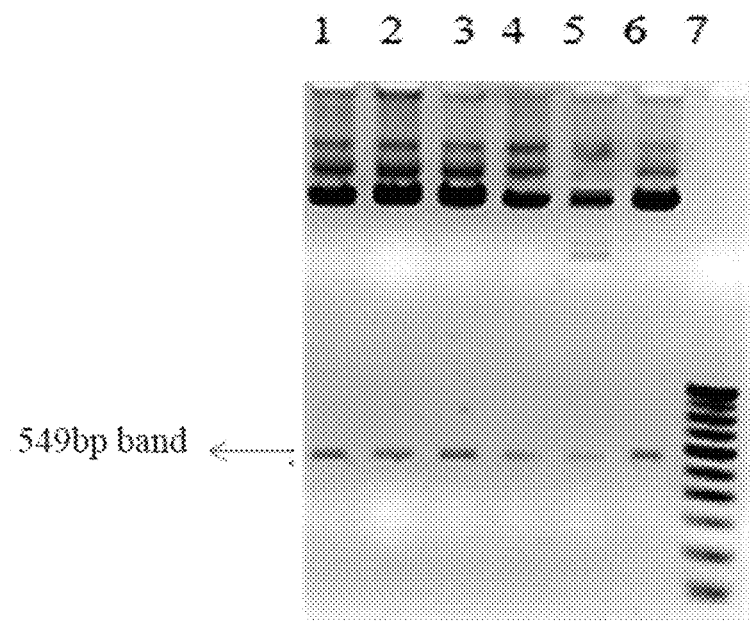
FIG. 4. The construct comprising sense and antisense orientation of 398 bp SPL5 transcript having a gus Intron. This expression cassette when transcribes produces a double stranded small interfering RNA (dsRNA) molecule. Lane 1, Sense strand digested with NcoI and BamHI, arrow shows desired 800 bp band. Lane 2, SPL5 sense and antisense strand digested with NcoI and SpeI resulting in desired 1.2 kb band. Lane 3 and 4 are negative clones. Lane 5 is 1 kb marker and lane 6 is 100 bp marker.

The 398 bp sequence of SPL5 having AscI and SwaI restriction enzyme site at 5' end and BamHI and SpeI at 3' end was cloned into $Sk^+$ vector. The knockdown module of SPL5 was made by first digesting with AscI and SwaI and this fragment was cloned into sense direction and Further to clone into antisense direction the construct was digested with BamHI and SpeI. These sense and antisense fragments were sub-cloned into Binary vector PFGC 1008 (of *Arabidopsis* Biological Resource Centre, Columbus, USA). The resultant PFGC 1008 carrying the knockdown module was transformed into cotton via *Agrobacterium tumefaciens* strain GV3101 following the modified protocol (Cangelosi et al., 1991) (FIG. 4).

Example 4

Transformation of Cotton Plants

Single isolated colony of *A. tumefaciens* LBA 4404 harboring binary vector containing kanamycin resistance gene for Overexpression and chloramphenicol for knockdown expression as selection marker was inoculated in YEB medium containing antibiotics streptomycin (250 µn/ml) rifampicin (50 µg/ml) and kanamycin (100 µg/ml) and grown (200 rpm, overnight, 28° C.). Fifty micro liters of the overnight culture was diluted to 100 ml in YEB medium and grown till $OD_{600}$ reached to 0.8. Cells were recovered by centrifugation in SS34 rotor (5,000 rpm, 10 min, 4° C.). The pellet was suspended in co-cultivation medium (MS salts, 2% glucose, 10 mM MES and 100 mM acetosyringone, pH 5.6) to $OD_{600}$ 0.6. Coker-312 seeds were surface sterilized with. 1% $HgCl_2$ solution for 5 minutes. Sterilized seeds were then finally kept in growtech under moist condition for germination. Germinated seeds were used for embryo transformation. Injuries were induced at arial meristemetic region via cut. Injured seeds were then finally incubated with bacterial cell, dissolved in MSO media having 100 uM Acetosyringone for overnight. After incubation with bacterial cell seeds were transferred in ½ MS media containing 0.2% phytagel and cocultivated for 2 days under dark condition. After co cultivation seeds were washed with cefotaxime (250 mg/l) to remove bacterial cells and transfer in test tube over paper Bridge containing ½ MS liquid media till it convert to plantlets. Plantlets then transferred to soil for hardening and then finally in glass house for proper growth.

Example 5

Figure 5:
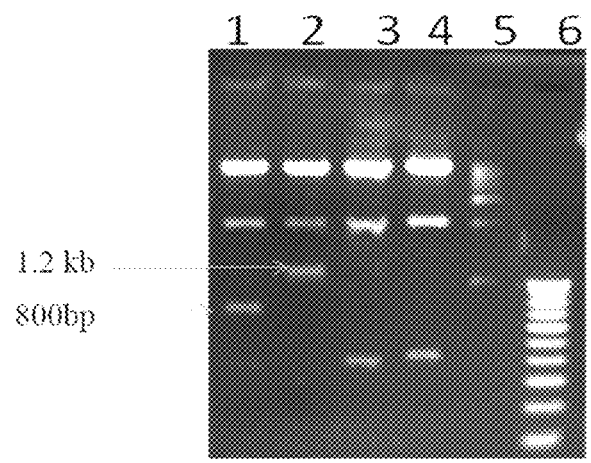
FIG. 5. PCR confirmation of transgenic plants by using hptII primer.
Figure 6:
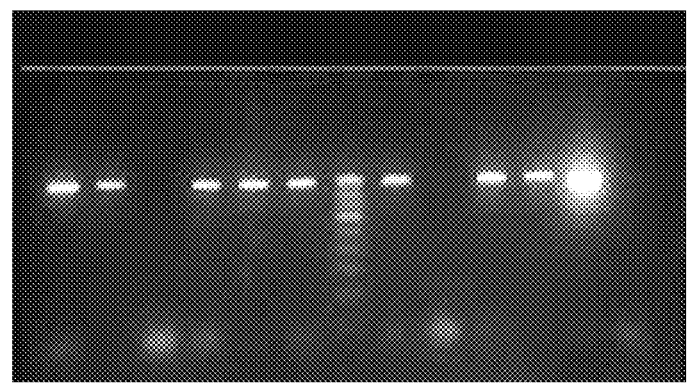
FIG. 6a-6b. Phenotypic analysis of transgenic cotton plants.
Figure 6:
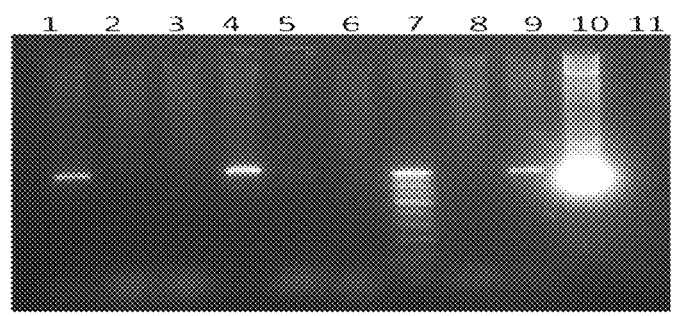
Figure 7:
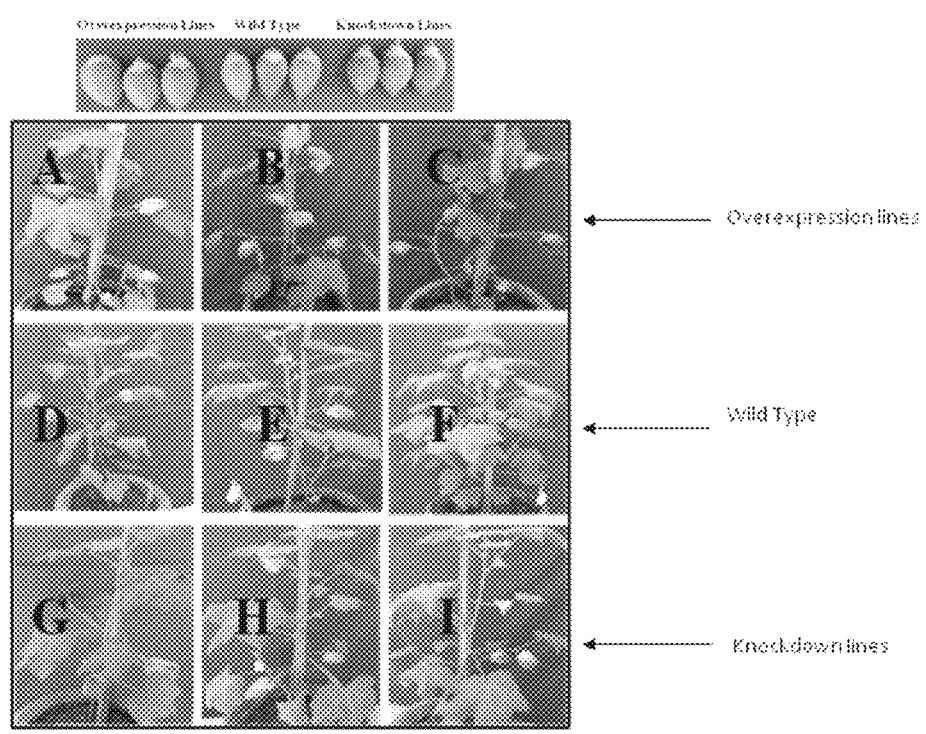
FIG. 7a. Comparison of the cotton bolls number in overexpression, knockout and wild type plants. Higher boll number and size (boll density) is shown in three (A, B and C) independent transgenic lines harbouring CaMV35S-SPL5 overexpression chimeric gene. Further G, H and I show low boll density whereas D, E and F are wild type plants. To differentiate the boll size the flowers were tagged in three different independent lines at 0 DPA of overexpression, knockdown and wild type plant. Interestingly, significant difference was seen at 19 DPA bolls.
FIG. 7b, represents yield of cotton bolls.

Analysis of Transgenic Lines for Transgene Integration and Phenotypic Evaluation Genomic DNA of the transgenic lines and control plant was isolated by CTAB method of DNA extraction. The genomic DNA was used as template to amplify a fragment of 900 bp hygromycin gene by using one set of primers of SEQ ID No: 5 i.e. 5'-ACACAGCCATCGGTCCAGAC-3' (Referred in Yang et al, Front. Agric. China 1(3):250-254, 2007) and SEQ ID NO: 6 i.e. 5'-GACGTCTGTCGA-GAAGTTTCTGA-3' (internal generated sequence). The PCR reaction consisted of 94° C. for 4 min, 94° C. for 1 min, 58° C. for 30 sec and 72° C. for 1 min, Go to 2 for 30 cycles 72° C. for 5 min. The desired band of 900 bp was obtained in the PCR of transgenic lines and positive control but not in control (Wild type) plants and negative control (without template). This experiment was repeated for three times for conformation (FIG. 5 and 6). T0 seeds from selected events were grown as segregating T1 populations in transgenic glass house. Fifty T0seeds of overexpression line and fifty T0 seeds of knockdown line were grown in soil pot in glass house. Six null plants lacking the transgene were also grown as a control. Since the plants were co-transformed with the hptll resistance gene as a selectable marker, only those plants will give PCR positive that carry the transgene. Fourteen overexpression and fourteen knockdown transgenic lines at T1 generation were found to be positive. Further, phenotypic evaluation determined that overexpression lines had ~5.8 boll/plant and ~5.8 gm lint/plant whereas knockdown lines had ~2.8 boll/plant and 3.2 gm lint/plant in compared to wild type (FIG. 7).

Advantages of the Invention

Boll number and boll size are the basic yield components of cotton. In order to improve the characteristics or yield of cotton fibre, a gene has been found whose regulated expression is associated with increased boll number, size and lint percentage. Hitherto there is no report to modulate the boll density by modifying a transgene in cotton.

We claim:

1. A method of producing transgenic cotton plants having increase in yield of boll number and boll size comprising steps of:
   (a) transforming cotton plant cells with a recombinant DNA construct comprising a promoter operably linked to the polynucleotide sequence of SEQ ID NO: 1 encoding the SPL5 protein of SEQ ID NO: 2, wherein the promoter is selected from the group consisting of FBP7, Actin, TA29; and CaMV 35S, and wherein said transforming is Agrobacterium mediated transformation;
   (b) regenerating transformed cotton plants from said transformed cotton plant cells overexpressing said SPL5 protein of SEQ ID NO: 2; and
   (c) selecting a transformed cotton plant obtained from step (b) which is transformed with said recombinant DNA construct, overexpresses said SPL5protein of SEQ ID NO: 2 and exhibits increase in yield of boll number and boll size as compared to a wild-type cotton plant species lacking said recombinant DNA construct.

2. The method of claim 1, wherein said Agrobacterium is strain GV3101.

* * * * *